United States Patent
Ando

(10) Patent No.: US 9,481,168 B2
(45) Date of Patent: Nov. 1, 2016

(54) DEVICE FOR DETECTING STATE OF DISCHARGED LIQUID DROPLET AND IMAGE-FORMING APPARATUS INCLUDING THE SAME

(71) Applicant: Hiroshi Ando, Ibaraki (JP)

(72) Inventor: Hiroshi Ando, Ibaraki (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/672,403

(22) Filed: Mar. 30, 2015

(65) Prior Publication Data

US 2015/0290929 A1    Oct. 15, 2015

(30) Foreign Application Priority Data

Apr. 11, 2014 (JP) .................... 2014-082080

(51) Int. Cl.

| | | |
|---|---|---|
| *B41J 29/393* | (2006.01) | |
| *B41J 29/38* | (2006.01) | |
| *B41J 2/045* | (2006.01) | |
| *B41J 2/165* | (2006.01) | |
| *B41J 2/21* | (2006.01) | |
| *G01N 21/47* | (2006.01) | |

(52) U.S. Cl.
CPC ......... *B41J 2/04586* (2013.01); *B41J 2/04561* (2013.01); *B41J 2/16579* (2013.01); *B41J 2/16585* (2013.01); *B41J 2/2142* (2013.01); *B41J 2/2146* (2013.01); *G01N 21/4788* (2013.01)

(58) Field of Classification Search
CPC  B41J 2/16579; B41J 2/04561; B41J 2/0451; B41J 29/393; B41J 2/2142; B41J 2/125; B41J 2/2146; B41J 29/38

USPC ................................................ 347/9, 14, 19
See application file for complete search history.

(56) References Cited

U.S. PATENT DOCUMENTS

| | | | | |
|---|---|---|---|---|
| 2002/0186268 A1* | 12/2002 | Endo | .................... | B41J 2/16508 347/19 |
| 2007/0064041 A1* | 3/2007 | Sugahara | ................. | B41J 3/543 347/19 |

(Continued)

FOREIGN PATENT DOCUMENTS

JP      2008-162148      7/2008

OTHER PUBLICATIONS

U.S. Appl. No. 14/577,105, filed Dec. 19, 2014.

(Continued)

*Primary Examiner* — Jannelle M Lebron
(74) *Attorney, Agent, or Firm* — Oblon, McClelland, Maier & Neustadt, L.L.P

(57) ABSTRACT

A device for detecting a state of a discharged liquid droplet includes a plurality of nozzles which is arranged in a width direction of a recording medium orthogonal to a feeding direction of the recording medium to discharge a liquid droplet toward the recording medium, a light emitter which is provided on one side of the recording medium in the width direction orthogonal to the feeding direction of the recording medium, and a light receiver which is provided on the other side of the recording medium in the width direction, wherein the light emitter includes a light-emitting element, a condenser lens which condenses light from the light-emitting element to emit as a light beam, and an aperture stop member including an aperture opening through which the light beam passes.

9 Claims, 8 Drawing Sheets

(56) References Cited

U.S. PATENT DOCUMENTS

| | | | |
|---|---|---|---|
| 2008/0106590 A1* | 5/2008 | Koizumi | B41J 2/451 347/238 |
| 2009/0091595 A1* | 4/2009 | Hayashi | B41J 2/2142 347/19 |
| 2009/0322823 A1* | 12/2009 | Ito | B41J 2/16579 347/20 |
| 2013/0147874 A1 | 6/2013 | Andoh | |
| 2015/0009252 A1 | 1/2015 | Andoh et al. | |

OTHER PUBLICATIONS

U.S. Appl. No. 14/620,005, filed Feb. 11, 2015.

* cited by examiner

DEVICE FOR DETECTING STATE OF DISCHARGED LIQUID DROPLET AND IMAGE-FORMING APPARATUS INCLUDING THE SAME

CROSS-REFERENCE TO RELATED APPLICATION

The present application is based on and claims priority from Japanese Patent Application Number 2014-082080, filed Apr. 11, 2014, the disclosure of which is hereby incorporated by reference herein in its entirety.

BACKGROUND

1. Field of the Invention

The present invention relates to a device for detecting a state of liquid droplets discharged from a nozzle of a recording head, and an image-forming apparatus incorporating such a device.

2. Description of the Related Art

Serial type image-forming apparatuses and line type image-forming apparatuses are well known. The serial type image-forming apparatus is configured to discharge liquid droplets toward a recording paper from a nozzle of a recording head while moving the recording head in a main-scanning direction which is orthogonal to a sub-scanning direction of a feeding direction of the recording paper as a recording medium. The line type image-forming apparatus is configured to discharge liquid droplets toward a recording paper from nozzles of a plurality of recording heads fixed in the main-scanning direction while feeding the recording paper in the sub-scanning direction.

In these types of image-forming apparatuses, a discharge error of the nozzle may occur due to an increase in ink viscosity and ink solidification arising from evaporation of solvent from a nozzle hole, dust attachment to the nozzle hole, bubble interfusion into ink or the like. Image quality is degraded when such a discharge error occurs.

In view of this, these types of image-forming apparatuses are provided with a device for detecting a state of liquid droplets discharged from a recording head (refer to Patent Document 1: JP4925184B). This device determines the presence or absence of a discharged liquid droplet, and includes a light emitter which is provided on one side of a recording paper in the width direction orthogonal to the feeding direction of the recording paper, and a light receiver which is provided on the other side of the recording paper in the width direction.

The light emitter includes a light-emitting element, collimator lens, and aperture stop member. A square aperture opening is formed in the aperture stop member.

Light from the light-emitting element is condensed by the collimator lens, and passes through the aperture opening of the aperture stop member as light beams to irradiate the light receiver. A light-receiving surface of the light receiver is displaced in the feeding direction of a paper relative to the optical axis (optical axis of light-receiving element) of the light emitter.

This device receives scattered light of light beams with the light receiver, which scatters forward in the traveling direction of the light beams due to the existence of the liquid droplets, to thereby determine presence or absence of a liquid droplet by the output of the light receiver. Also, this device reduces the attachment of the mist, which is generated upon the discharge of liquid droplets, to the light-emitting element and the collimator lens.

In the device described in the above document, when the light beams pass through the aperture opening, diffracted light with the light beams is generated in the direction of the line segments connecting respective middle points of the parallel two sides of the aperture opening.

For this reason, when the light-receiving surface of the light receiver is displaced in the direction of the line segment connecting the respective middle points of the two sides, the amount of diffracted light which is incident on the light-receiving surface as offset light increases, noise relative to the amount of scattered light due to liquid droplets relatively increases, and the detection accuracy of the state of the discharged liquid droplets is lowered due to an increase in S/N ratio.

SUMMARY

The present invention has been made in view of the above circumstances, and it is an object of the present invention to provide a device for detecting a state of a discharged liquid droplet which improves detection accuracy of a state of a discharged liquid droplet while preventing attachment of mist to a light-receiving element and a lens.

To achieve the above object, an aspect of the present invention provides a device for detecting a state of a discharged liquid droplet including a plurality of nozzles which is arranged in a width direction of a recording medium orthogonal to a feeding direction of the recording medium to discharge a liquid droplet toward the recording medium, a light emitter which is provided on one side of the recording medium in the width direction orthogonal to the feeding direction of the recording medium, and a light receiver which is provided on the other side of the recording medium in the width direction, wherein the light emitter includes a light-emitting element, a condenser lens which condenses light from the light-emitting element to emit as a light beam, and an aperture stop member including an aperture opening through which the light beam passes, the aperture opening has a rhombic shape or a rectangular shape, and a light-receiving surface of the light-receiving element is displaced in the feeding direction of the recording medium, and is displaced on extension lines of diagonal lines of a light beam of the rhombic shape or the rectangular shape of which a contour is defined through the rhombic or rectangular aperture opening.

BRIEF DESCRIPTION OF THE DRAWINGS

The accompanying drawings are included to provide further understanding of the invention, and are incorporated in and constitute a part of this specification. The drawings illustrate embodiments of the invention and, together with the specification, serve to explain the principle of the invention.

FIG. 10 illustrates a state where diffracted light is generated in a direction at a tilt to a diagonal line parallel to the feeding direction.

DETAILED DESCRIPTION OF THE PREFERRED EMBODIMENTS

Figure 1:
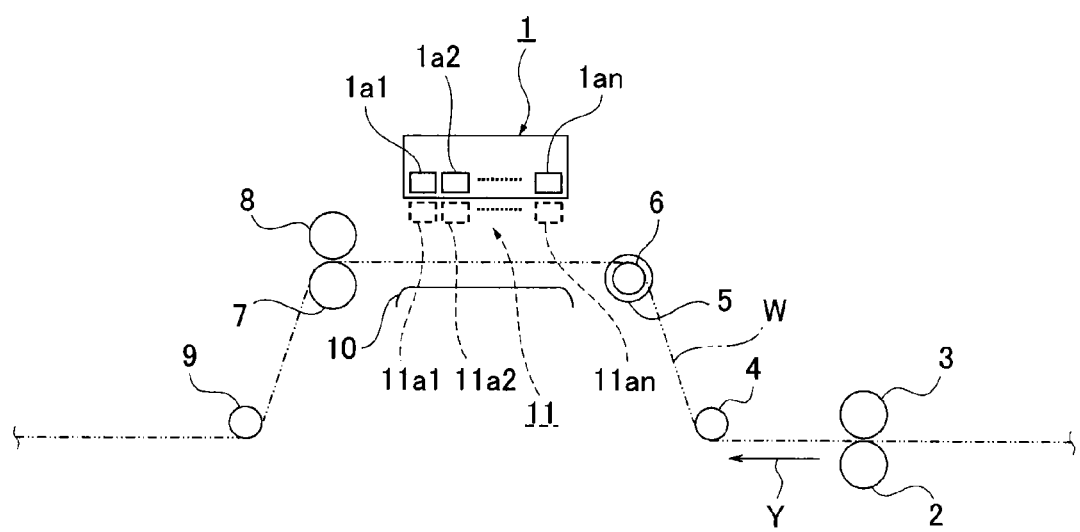
FIG. 1 is a view schematically showing a configuration of an image-forming apparatus incorporating a discharged liquid droplet-detecting device according to an embodiment of the present invention.

FIG. 1 is a view schematically showing a configuration of an image-forming apparatus (inkjet type printer) according to an embodiment of the present invention.

Referring to FIG. 1, reference number 1 denotes a recording head array, and W denotes a recording paper (recording medium). In the image-forming apparatus, a paper-feeding roller 2, a driven roller 3 which rotates by the paper-feeding roller 2, a tension roller 4, a driven roller 6 including an encoder 5 which detects the feeding amount of the recording paper W, a paper discharge roller 7, a driven roller 8 which rotates by the paper discharge roller 7, and a tension roller 9 are appropriately provided in the paper-feeding direction Y of the recording paper W. The paper discharge roller 7 rotates by a not-shown driving motor.

A running plate 10 is provided between the driven roller 6 and the paper discharge roller 7. The recording paper W is fed while being guided by the running plate 10. The recording head array 1 is disposed opposite to the running plate 10 to sandwich the recording paper W therebetween.

A plurality of inkjet heads (recording head) 1a1, 1a2, . . . , 1an is arranged in the recording head array 1 in the feeding direction Y of the recording paper W. A plurality of nozzles is arranged in the inkjet heads 1a1, 1a2, . . . , 1an in the width direction orthogonal to the feeding direction Y of the recording paper W.

The recording paper W is fed on the downstream side in the feeding direction by the paper discharge roller 7 and the driven roller 8, receives liquid droplets while crossing the running plate 10, and is discharged while being printed. In addition, in this embodiment, the encoder 5 is provided in the driven roller 6, but the encoder 5 may be provided in the driven roller 8.

The material of the recording paper W is not limited to paper. It includes a medium such as a string, fiber, cloth, fabric, leather, metal, plastic, glass, and ceramics and an OHP sheet, etc. The term recording paper W is used as a generic term for a material on which ink is attached as liquid droplets.

Printing and image formation are intended not only to form characters or figures, etc. on the recording paper W but also to form an image such as patterns, etc. on the recording paper W, to attach liquid droplets on the recording paper W, and to form a three-dimensional object by attaching liquid droplets on the recording paper W. Additionally, the term ink is used as a generic term for recording liquid, fixing processing liquid, and resin, etc.

Next, a schematic configuration of a discharged liquid droplet-detecting device will be described. A discharged liquid droplet-detecting device 11 is provided between the recording head array 1 and the running plate 10. The discharged liquid droplet-detecting device 11 is provided in each of the inkjet heads 1a1, 1a2, . . . 1an. Reference numbers 11a1, 11a2, . . . , 11an are applied to the respective discharged liquid droplet-detecting devices 11 in accordance with the respective inkjet heads 1a1, 1a2, 1an.

Figure 2:
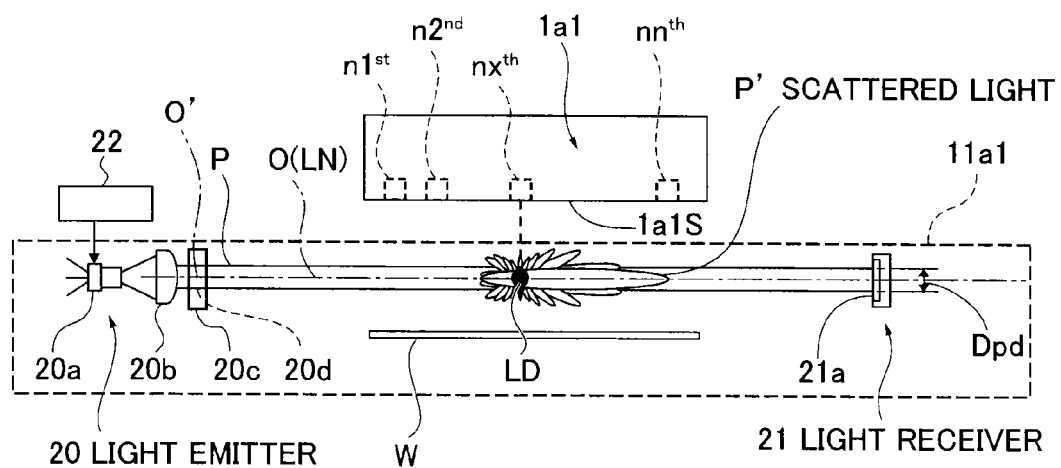
FIG. 2 is a side view schematically showing a first discharged liquid droplet-detecting device illustrated in FIG. 1 along a feeding direction of a recording medium.

FIG. 2 illustrates the discharged liquid droplet-detecting device 11a1 corresponding to the inkjet head 1a1. As illustrated in FIG. 2, n-nozzles $n1^{st}$, $n2^{nd}$, ..., $nx^{th}$, $nn^{th}$ are arranged in the inkjet head 1a1 in the width direction of the recording paper W, which is orthogonal to the feeding direction Y of the recording paper W.

Figure 3:
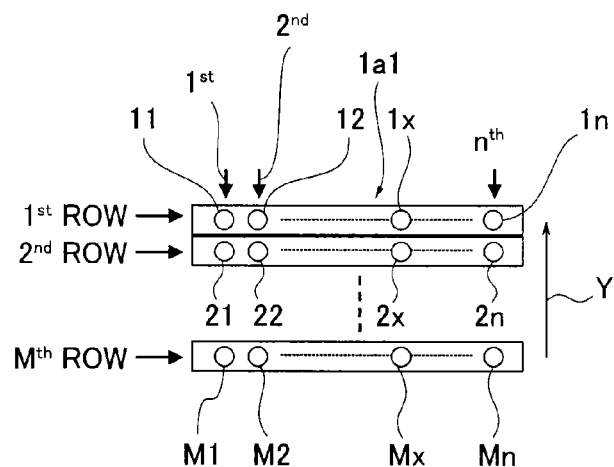
FIG. 3 is a plan view schematically showing an arrangement state of nozzles of the discharged liquid droplet-detecting device illustrated in FIG. 2.

M-nozzle rows (n is integral number from 1 to M) are provided in the inkjet head 1a1 in the feeding direction Y of the recording paper W. One nozzle row includes nozzles $n1^{st}$, $n2^{nd}$, ..., $nx^{th}$, $nn^{th}$. Reference numbers, 11, 12, ..., 1x, ..., 1n, 21, 22, ..., 2x, ... 2n, M1, M2, ..., Mx, ..., Mn are applied to the respective nozzles in FIG. 3.

The discharged liquid droplet-detecting device 11a1 includes a light emitter 20 and a light receiver 21. The light emitter 20 is provided on one side of the recording paper W in the width direction orthogonal to the feeding direction Y, and the light receiver is provided on the other side of the recording sheet W in the width direction. The light emitter 20 includes a light-emitting element 20a, condenser lens 20b, and aperture stop member 20c. Note that the light-emitting element 20a includes a semiconductor laser, but the light-emitting element 20 is not limited to a semiconductor laser. The light-emitting element 20a may include, for example, an LED (Light-Emitting Diode). The semiconductor laser is driven by a laser driver 22.

Figure 4:
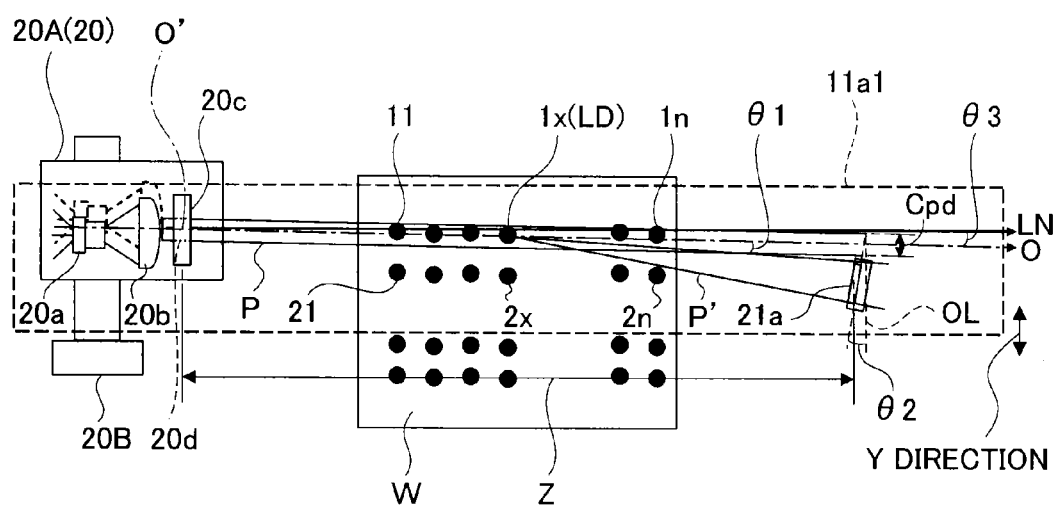
FIG. 4 is an overhead view showing the discharged liquid droplet-detecting device illustrated in FIG. 2.

The light emitter 20 includes a light-emitting unit 20A, as illustrated in FIG. 4. The light-emitting unit 20A reciprocates by a movement mechanism 20B in the feeding direction Y of the recording paper W. The condenser lens 20b condenses the light from the light-emitting element 20a to emit as a light beam P.

The condenser lens 20b is a collimator lens, and the light beam P is a parallel light flux. However, the light beam P may be the after-described convergent light. In FIGS. 2, 4, a liquid droplet LD is discharged from the nozzle $1x^{th}$.

Figure 5:
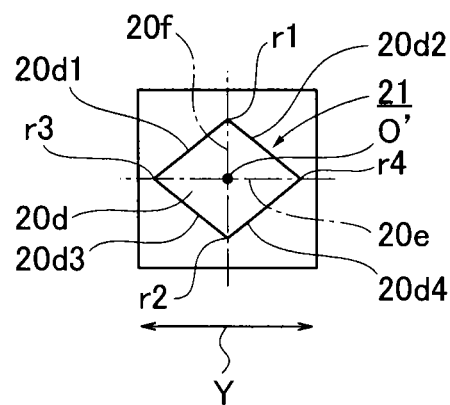
FIG. 5 is a plan view showing an aperture stop member illustrated in FIG. 2.

A rhombic aperture opening 20d through which the light beam P passes is formed in the aperture stop member 20c, as illustrated in FIG. 5. Note that the rhombic aperture opening 20d is illustrated in FIG. 5, but a square or rectangular aperture opening 20d may be used.

The rhombic aperture opening 20d includes four apexes r1, r2, r3, r4. The rhombic aperture opening 20d includes one diagonal line 20e connecting the apexes r3, r4, and the other diagonal line 20f connecting the apexes r1, r2, which is orthogonal to the diagonal line 20e. The aperture opening 20d includes the respective sides 20d1 to 20d4. The length of each side 20d1 to 20d4 is represented as a, the length of the diagonal line 20e is represented as c, and the length of the diagonal line 20f is represented as d (refer to FIG. 16).

The diagonal line 20e is parallel to the feeding direction Y of the recording paper W, and the diagonal line 20f is vertical to a head nozzle surface 1a1S (refer to FIG. 2) of the inkjet head 1a1 and the recording paper W.

The liquid droplet LD is appropriately discharged from the respective nozzles $n1^{st}$, $n2^{nd}$, ..., $nx^{th}$, ..., $nn^{th}$ according to image data, and the light beam P is scattered by the liquid droplet LD while passing through the respective nozzles to be scattered light P'.

The light receiver 21 includes a light-receiving element such as a photodiode. In FIGS. 2, 4, reference number 21a denotes a light-receiving surface.

A contour shape of the light beam P is defined by the aperture opening 20d. The width of the light beam P is defined by the diagonal lines 20e, 20f. The beam width defined by the diagonal line 20f is represented as a longitudinal direction beam width Dpd, and the beam width defined by the diagonal line 20e is represented as a lateral direction beam width Cpd.

As illustrated in FIG. 2, the optical axis O of the light beam P and the light-receiving surface 21a of the light-receiving element are vertical to the light beam P in section vertical to the feeding direction Y of the recording paper W. More specifically, the tilt angle of the optical axis O of the light beam P is 0 degrees to the nozzle arrangement direction LN (refer to FIG. 4).

The tilt angle of the optical axis O of the light beam P is θ3 to the arrangement direction LN of the nozzles 11, 12, ..., 1x, ..., 1n, which is parallel to the width direction of the recording paper W, as illustrated in FIG. 4 in a plane which is parallel to the feeding direction Y of the recording paper W.

The light-receiving surface 21a tilts to the optical axis O to be in an angle range of 0≤θ2≤θ1, where θ1 is an angle between an end portion of the light-receiving surface 21a on the side close to the optical axis O and the optical axis O, and θ2 is an angle between the light-receiving surface 21a and a straight line (straight line parallel to feeding direction Y) OL, which is vertical to the optical axis O.

Figure 6:
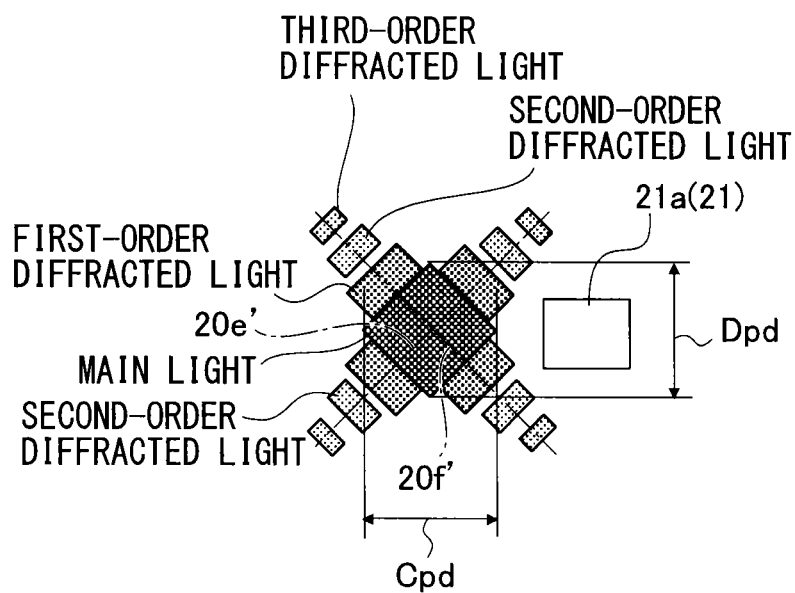
FIG. 6 is a view showing a relationship between a diffraction pattern of a light beam with the aperture stop member illustrated in FIG. 2 and a light-receiving surface of a light-receiving element from the optical axis direction of a light-emitting element.

As illustrated in FIG. 6, a part of the light beam P which is converted into a parallel light flux by the condenser lens 20b is diffracted when passing through the aperture opening 20d of the aperture stop member 20c. First-order diffracted light, second-order diffracted light, third-order diffracted light, ... are sequentially formed in the direction of line segments 20e', 20f' connecting the respective middle points of the respective sides 20d1 to 20d4 of the aperture opening 20d. A light beam (zero-order diffracted light) P passing through the aperture opening 20d without being diffracted is herein referred to as main light.

The light-receiving surface 21a is displaced from the optical axis O in the extension line direction of the diagonal line 20e (feeding direction Y of recording paper W), and is positioned such that the main light of the light beam P is not incident on the light-receiving surface 21a. In this case, the light-receiving surface 21a is displaced in the feeding direction Y at a width wider than the lateral direction beam width Cpd of the light beam P. In addition, the diffraction pattern of the light beam P shows a diffraction pattern which is formed on a not-shown virtual screen including the light-receiving surface 21a separated from the center of the aperture opening O' in the optical axis direction at a distance z (refer to FIG. 4).

The light-receiving element receives the scattered light P' of the light beam P, and photoelectrically converts the scattered light P'. The output voltage V by the light-receiving element is input to a not-shown measurement circuit.

The measurement circuit prepares light-receiving data based on the output voltage V, and detects the state of the liquid droplet discharged from the respective nozzles.

In addition, the ratio of the lateral direction beam width Cpd to the longitudinal direction beam width Dpd is appropriately determined in view of conditions such as the wavelength of the light beam P, the strength distribution, the intervals between respective nozzle rows, the distance from the liquid droplet LD to the light-emitting element 20a, the distance from the liquid droplet LD to the light-receiving surface 21a, the size of the light-receiving surface 21a of the light-receiving element, the arrangement position of the light-receiving element, and the distance between the inkjet head 1a1 and the recording paper W.

The aperture opening 20d having the diagonal lines 20e, 20f disposed in the longitudinal direction and the lateral direction has an advantage to noise over the aperture opening 20d having the sides 20d1 to 20d4 disposed in the longitudinal direction and the lateral direction. The reason will be described below.

Figure 7:
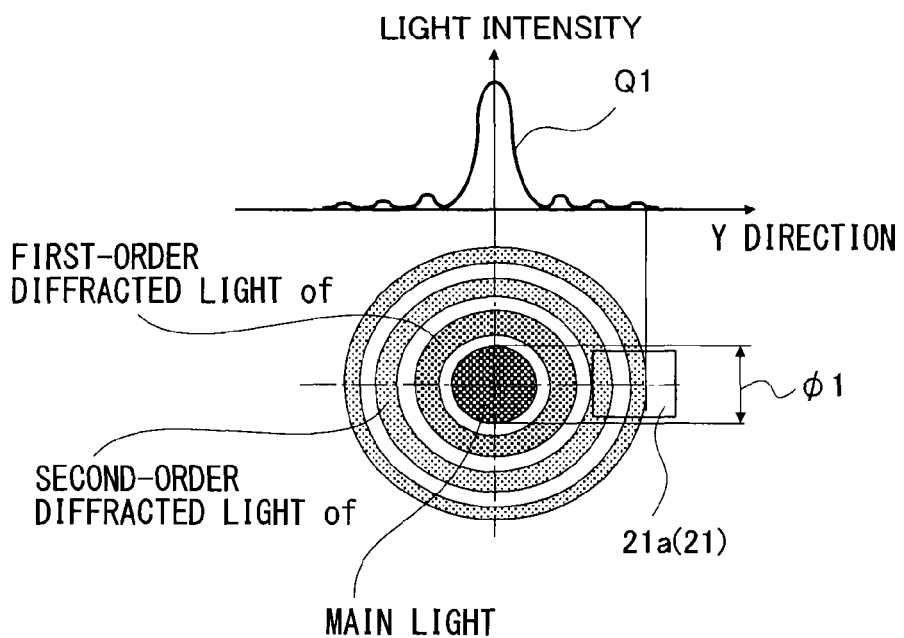
FIG. 7 is a view showing a relationship among a concentric diffraction pattern, which is generated when the aperture opening of the aperture stop member illustrated in FIG. 2 has a circular shape, its intensity distribution, and a diffraction pattern to the light-receiving surface of the light-receiving element.

FIG. 7 shows the pattern of the diffracted light of the light beam P and its intensity distribution when the aperture opening 20d has a circular shape.

When the aperture opening 20d has a circular shape, the diffracted light pattern is generated in a concentric fashion in accordance with Fraunhofer diffraction formula shown below. The concentric central light flux is main light, and the amount of light attenuates in accordance with an increase in diameter, and the first-order, second-order, . . . diffracted light is sequentially generated.

$$u(\rho 2,\phi 2,z)=R_0 \cdot 2J_1(ka\rho 2/z)/(ka\rho 2/z) \ R_0=j \cdot \exp(-jkz)/\lambda z \cdot (-j(k/2a) \cdot (\rho 2^2))u_0 \cdot \pi \cdot a^2 \quad \text{(Formula 1)}$$

Where, $J_1$ represents Bessel function of the first kind of first order, and Bessel function of m-order is as follows.

$$Jm(U)=j^{-m}/2\pi f^2 \pi o e j(mV+Uc_OsV)dV$$

Where, z represents a distance between optical axes from the opening center O' of the aperture opening 20d to the light-receiving surface 21a, k represents a unit vector in k-direction, j represents a unit vector in j-direction, λ represents a wavelength of a light beam, $x_2=\rho_2 \cdot \cos\phi_2$, and $y_2=\rho_2 \cdot \sin\phi_2$. Where, $x_2$, $y_2$ represent positional coordinates in the plane orthogonal to the optical axis direction.

Additionally, ρ represents a radius of an area disk and ρ=0.610λ/NA, and NA represents the number of openings and NA=a/Z=sinθ.

When the light-receiving surface 21a is displaced at the diameter φ1 of the main light in the radial direction from the optical axis (center) O of the main light, the first-order diffracted light or more may be incident on the light-receiving surface 21a of the light-receiving element as offset light Of. In this case, the second-order diffracted light or more is incident on the light-receiving surface 21a for descriptive purposes.

Figure 8:
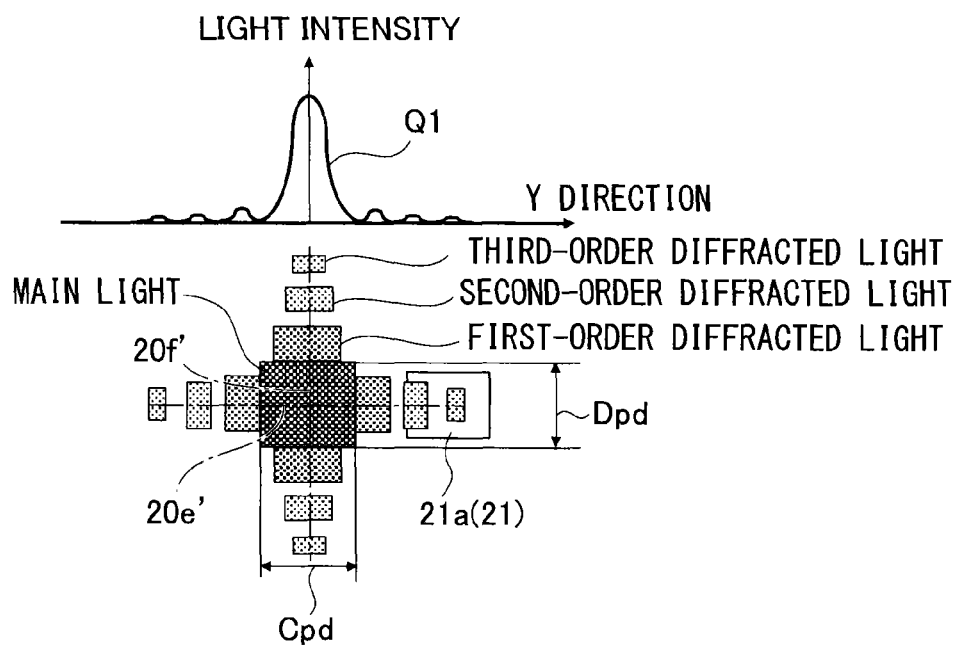
FIG. 8 is a view showing a relationship among a diffraction pattern, which is generated when the direction of the line segments connecting the middle points of the respective sides of the aperture stop member including the rectangular aperture opening illustrated in FIG. 5 is parallel to the feeding direction, its intensity distribution, and a diffraction pattern to the light-receiving surface of the light-receiving element, and also shows a state where a part of diffracted light illuminates the light-receiving surface of the light-receiving element.

FIG. 8 shows the diffraction pattern of the light beam P and its intensity distribution when the aperture opening 20d has a rectangular shape. In addition, for the purpose of illustration, the aperture opening 20d has a square shape.

When the aperture opening 20d has a square shape (generally, rectangular or rhombic shape), the diffraction pattern is generated in the directions of the line segments 20e', 20f connecting the middle points of the respective sides 20d1 to 20d4 in accordance with the Fraunhofer diffraction formula shown in the following formula 2. That is, a part of the concentric diffracted light becomes a diffraction pattern shape cut by the respective sides.

In FIG. 8, the central light flux is the main light, the central light flux attenuates, and the first-order, second-order, . . . diffraction light are sequentially generated in accordance with an increase in a distance from the main light flux.

$$U(x,y,z)=R_0 \cdot a \cdot a \cdot \sin c(ax/\lambda z) \cdot \sin c(ay/\lambda z) \ R_0= j \cdot \exp(-jkz) \cdot \exp(-j(k/2z) \cdot (x^2+y^2)) \times u\sin c(X)= \sin(\pi X)/(\pi X) \ x=(n+1) \cdot \lambda \cdot z/a, y=(n+1) \cdot \lambda \cdot z/\lambda \quad \text{(Formula 2)}$$

Where, X represents a variable number other than x, a represents a length of one side of the square opening, and x, y represent positional coordinates in a plane orthogonal to the optical axis direction.

More specifically, the diffracted light by the light beam P is generated in the direction of the line segments 20e', 20f connecting the middle points of the parallel two sides 20d1 to 20d4 of the aperture opening 20d. Even when the light-receiving surface 21a is displaced at the lateral direction beam width Cpd of the main light in the directions of the light segments 20e', 20f connecting the two sides from the optical axis (center) O of the main light, the first-order diffracted light or more is incident on the light-receiving surface 21a of the light-receiving element as offset light Of.

In addition, the strength distribution of the diffracted light is schematically shown in FIG. 7 and FIG. 8. The strength distribution changes according to the respective optical properties of the light-emitting element, condenser lens, and aperture stop member, and the distance from the condenser lens to the liquid droplet. In addition, Q1 denotes the intensity of the main light in FIGS. 7, 8.

An inconvenience occurs due to the incident of the offset light on the light-receiving surface 21a. The reason will be described below.

Upon an increase in angle θ1 illustrated in FIG. 4, the sum of the amount of the offset light Of, which is incident on the light-receiving surface 21a of the light-receiving element, and the amount of the scattered light P' is decreased. Consequently, the output voltage V of the light-receiving element changes according to the angle θ1, as illustrated in FIG. 9.

On the other hand, when the angle θ1 is a predetermined angle (saturation limit angle) of θ min or below, the offset light Of such as the reflected light of the light beam P, which is reflected by the recording paper W, and the reflected light of the light beam P, which is reflected by the nozzle surface 1a1S of the inkjet head 1a1, etc., in addition to the offset light Of caused by the diffracted light, is incident on the light-receiving surface 21a.

Figure 9:
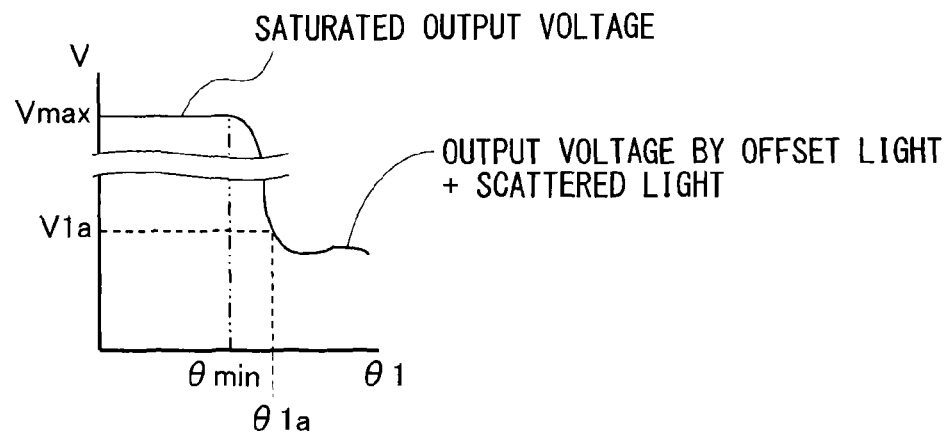
FIG. 9 is a graph showing a change degree of output voltage with a tilt of the light-receiving surface of the light-receiving element relative to the optical axis of the light-receiving element when the aperture stop member including the circular aperture opening illustrated in FIG. 7 is used or the aperture stop member including the rectangular aperture opening is disposed as illustrated in FIG. 8.

For this reason, the output voltage V of the light-receiving element is saturated, as illustrated in FIG. 9. When the output voltage V of the light-receiving element is saturated without discharging liquid droplets from nozzles, a change in the amount of the scattered light P' by the discharge of the liquid droplet LD cannot be detected.

When the angle θ1 is equal to a predetermined angle θ min or below, the presence and absence of the discharged liquid droplet LD cannot be detected. It is therefore necessary for the angle θ1 to fulfill the condition θ1≥θ min. In FIG. 9, the output voltage V when the angle θ1=θ1a is represented as V1a, and the output voltage V when the angle θ1≤θ min is represented as a saturated output voltage V max.

Note that the angular dependence properties of the output voltage V relative to the angle θ1 illustrated in FIG. 9 change according to the shape and size of the aperture opening 20d, the positional relationship between the aperture stop member 20c and the inkjet head 1a1, and the shape and size of a liquid droplet. FIG. 9 shows only an example.

Next, the reason that the aperture opening 20d including the diagonal lines 20e, 20f disposed in the longitudinal direction and the lateral direction has an advantage to noise will be described with reference to FIG. 10.

Figure 10:
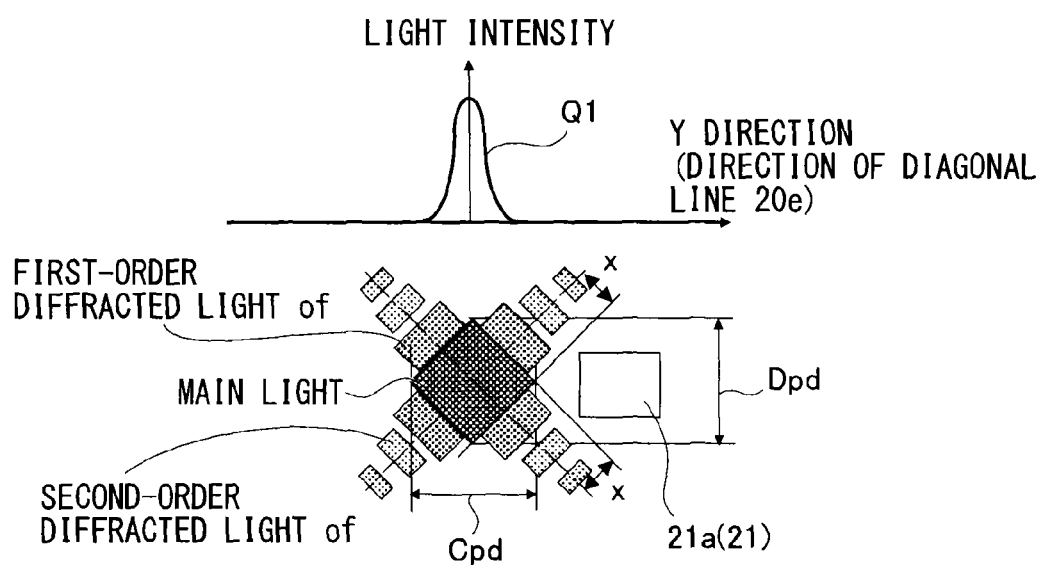
FIG. 10 is a view showing a relationship among a diffraction pattern of a light beam with the aperture stop member illustrated in FIGS. 2, 5, its strength distribution, and a diffraction pattern to the light-receiving surface of the light-receiving element.

FIG. 10 shows the diffraction pattern and the strength distribution of the light beam P of the direction of the diagonal line 20e.

Figure 11:
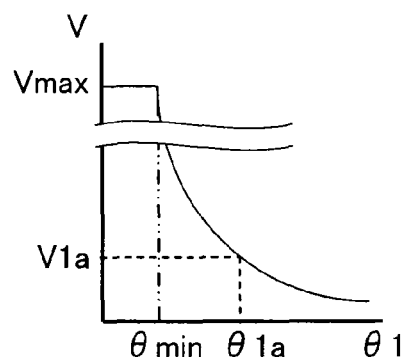
FIG. 11 is a graph showing a change degree of output voltage due to a tilt of the light-receiving surface of the light-receiving element relative to the optical axis of the light-receiving element when the aperture stop member including the rectangular aperture opening is disposed as illustrated in FIG. 10.

As illustrated in FIG. 10, when the light-receiving surface 21a is separately disposed in the extension direction of the diagonal line 20e of the aperture opening 20d, the main light is mostly prevented from being incident on the light-receiving surface 21a. Since the first-order diffracted light, second-order diffracted light, . . . are generated in the oblique direction, the diffracted light as the offset light Of is mostly prevented from being incident on the light-receiving surface 21a, compared to the aperture opening 10a disposed as illustrated in FIG. 8. Accordingly, as illustrated in FIG. 11, it is possible to reduce the predetermined angle θ min, and it is possible to mount the light-receiving element to be close to the light beam P.

Moreover, the diffracted light is generated in the direction oblique to the direction of the line segment vertically connecting the inkjet head 1a1 and the recording paper W. Thus, the amount of the reflected light as the offset light OF from the nozzle surface 1a1S of the inkjet head 1a1 by the diffracted light and the amount of the reflected light as the offset light Of from the recording paper W are reduced.

More specifically, as illustrated in FIG. 2, when the respective sides 20d1, 20d4 of the aperture opening 20d are disposed parallel to the nozzle surface 1a1S of the inkjet head 1a1, the diffracted light is generated in the direction vertical to the head nozzle surface 1a1S of the inkjet head 1a1, and the distance L' required for the diffracted light to reach the head nozzle surface 1a1S from the optical axis O is reduced. Thus, the diffracted light reflected by the head nozzle surface 1a1S is low-order diffracted light with small attenuation.

The amount of reflected light of the diffracted light is relatively larger than the amount of the reflected light of the diffracted light which is reflected by the nozzle surface 1a1S of the inkjet head 1a1 when the diagonal line 20e of the aperture opening 20d is disposed to be parallel to the nozzle surface 1a1S of the inkjet head 1a1. This is the same as the amount of reflected light from the recording paper W.

Figure 13:
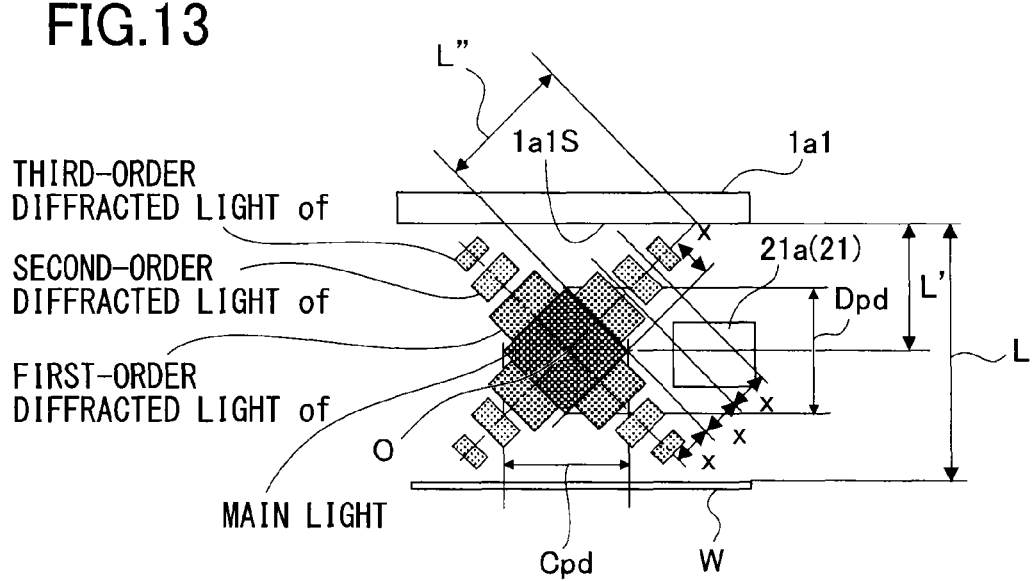
FIG. 13 is a view showing diffracted light as offset light, which is reflected from a nozzle surface of an inkjet head, and diffracted light as offset light, which is reflected from a recording medium, when the aperture stop member including the rectangular aperture opening is disposed as illustrated in FIG. 10.

On the other hand, as illustrated in FIG. 13, when the first diagonal line 20e of the aperture opening 20d is disposed to be parallel to the nozzle surface 1a1S of the inkjet head 1a1, the distance L" required for the diffracted light to reach to the head nozzle surface 1a1S from the optical axis O becomes √2L'. Thus, high-order diffracted light with large attenuation is reflected by the nozzle surface 1a1S.

Figure 12:
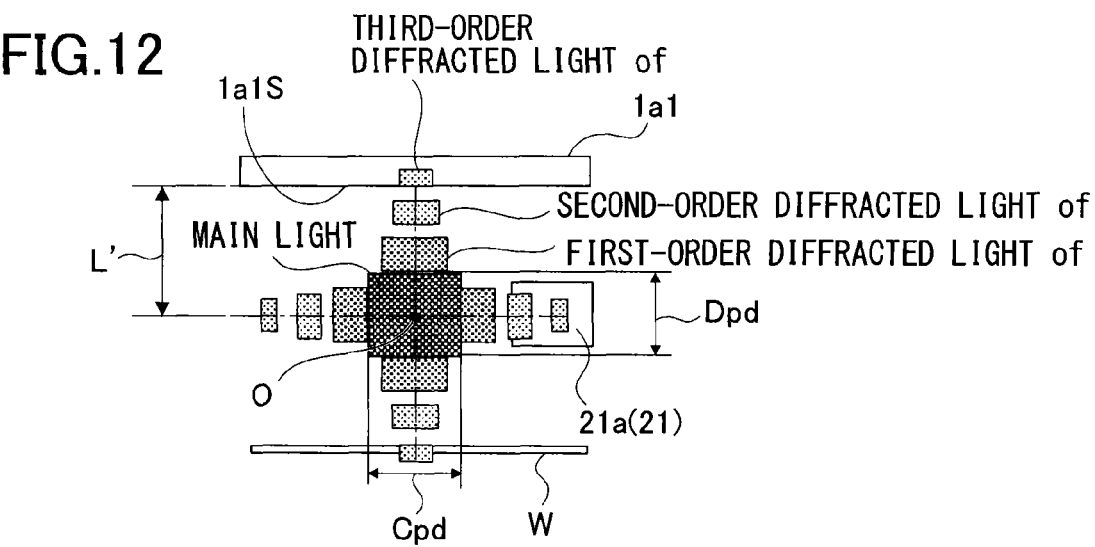
FIG. 12 is a view showing diffracted light as offset light, which is reflected from a nozzle surface of an inkjet head, and diffracted light as offset light, which is reflected from a recording medium, when the aperture stop member including the rectangular aperture opening is disposed as illustrated in FIG. 8.

Consequently, the amount of reflected light of the diffracted light which is reflected by the head nozzle surface 1a1S is smaller than the amount of reflected light when the aperture opening 20d is disposed as illustrated in FIG. 12. The saturation limit angle θ min with which the sum of the amount of the scattered light P' and the amount of the offset light Of is saturated decreases.

Figure 14:
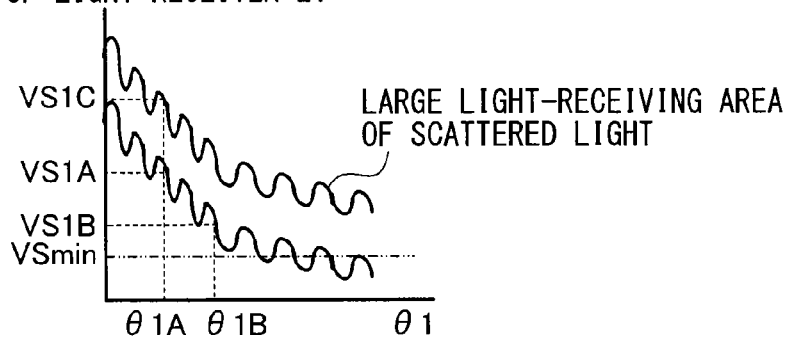
FIG. 14 is a graph showing an output property of the light-receiving element with scattered light from liquid droplets, and also is a graph showing a change degree of output voltage with a tilt of the light-receiving surface of the light-receiving element to the optical axis of the light-emitting element.

FIG. 14 is a graph showing a relationship between the angle θ1 and the output voltage V by the amount of scattered light P'. The amount of scattered light P' has an angular dependence property, which attenuates while maintaining a waveform.

In FIG. 14, the output voltage V=VSmin is a threshold, and it is not possible to detect the amount of scattered light P' with the output voltage V of the threshold or below. VS1B corresponding to the angle θ1B represents output voltage when the sides 20d1, 20d4 of the aperture opening 20d are disposed to be parallel to the nozzle surface 1a1S of the inkjet head 1a1. VS1A corresponding to the angle θ1A represents output voltage when the diagonal line 20e of the aperture opening 20d is disposed to be parallel to the nozzle surface 1a1S of the inkjet head 1a1. VS1C corresponding to the angle θ1A represents output voltage when the area of the light-receiving surface 21a is increased.

Figure 15:
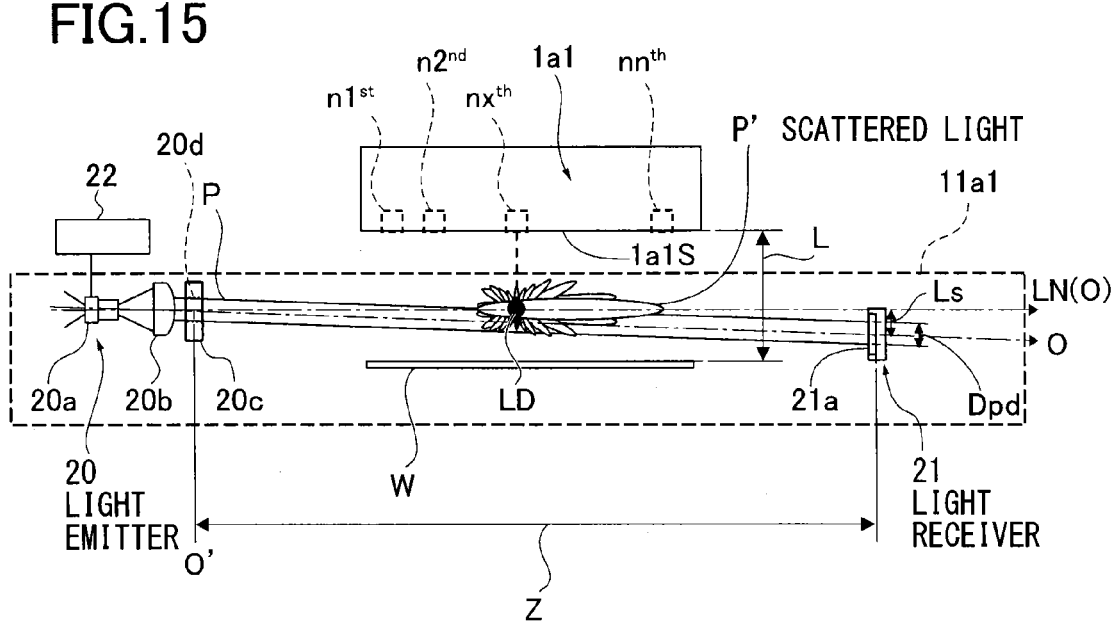
FIG. 15 is a view describing a condition in which a light beam passes between the recording medium and the inkjet head.

FIG. 15 shows one example for determining the aperture opening 20d of the aperture stop member 20c. The optical axis O of the light-emitting element 20a tilts to the head nozzle surface 1a1S, and the center of the light-receiving surface 21a is displaced at LS (displacement) from a position with no tilt of the optical axis O in the light-receiving position (position separated at distance z in optical axis direction from center O' of aperture opening 20d). The interval between the head nozzle surface 1a1S and the recording paper W is represented as L.

In order to design a compact device while preventing the incidence of the main light of the light beam P, the amount of reflected light caused by the diffracted light, the main light from the recording paper W, and the reflected light caused by the diffracted light on the light-receiving surface 21a of the light-receiving element as much as possible, it is preferable to set the size of the aperture opening 20d of the aperture member 20c as follows.

The interval between the inkjet head and the recording paper W is represented as L, as illustrated in FIG. 13. The longitudinal direction beam width is represented as Dpd and the lateral direction beam width is represented as Cpd. The interval L is determined based on the liquid droplet LD and the inkjet head 1a1.

In order to reduce the amount of offset light Of caused by the main light of the light beam P, the reflected light from the inkjet head 1a1 with the diffracted light, and the reflected light from the recording paper W, it is necessary to pass the main light of the light beam P and the diffracted light between the nozzle surface 1a1S and the recording paper W from one side to the other side, such that the main light of the light beam P and the diffracted light do not illuminate the recording paper W and the nozzle surface 1a1S. In view of the displacement LS of the light-receiving element from the optical axis O of the tilt 0 of the light-emitting element, the following condition (1) is obtained.

$$Dpd \leq L - LS \tag{1}$$

Figure 16:
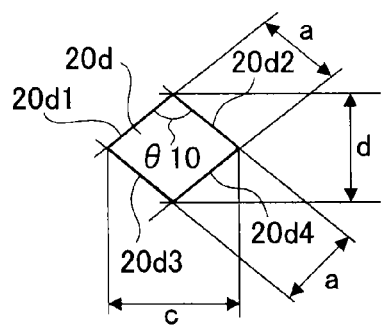
FIG. 16 is a plan view showing the aperture stop member when the aperture opening has a rhombic shape.

As described above, the length of each side which defines the aperture opening 20d of the aperture stop member 20 is represented as a, the diagonal line length corresponding to the lateral direction beam width Cpd of the light beam P is represented as c, and the diagonal line length corresponding to the longitudinal direction beam width Dpd of the light beam P is represented as d (refer to FIG. 16).

Where the shape of the main light of the light beam P is the same as the contour shape of the aperture opening 20d of the aperture stop member in a virtual screen having a light-receiving surface, based on Pythagorean Theorem, the following equation is obtained.

$$(Dpd/2)^2 + (Cpd/2)^2 = (2x)^2 \; Dpd = (16x^2 - Cpd^2)^{1/2} \tag{2}$$

Where an angle between the side 20d1 and the side 20d2 of a rhombic shape is θ10, based on a sine equation, the following equation is obtained.

$$Cpd/2 = 2 \cdot x \cdot \sin(\theta 10/2)$$

Thus, the following equation is obtained.

$$Cpd = 4 \cdot x \cdot \sin(\theta 0/2) \tag{3}$$

When the above equation (3) is substituted into the above equation (2), the following equation is obtained.

$$\begin{aligned} Dpd &= \left(16x^2 - (4 \cdot x \cdot \sin(\theta 10/2))^2\right)^{1/2} \\ &= \left(16x^2 - 16x^2((1 - \cos(2 \cdot \theta 10/2))/2\right)^{1/2} \\ &= 4x((1 - \cos(\theta 10))/2)^{1/2} \end{aligned} \tag{4}$$

Based on the Fraunhofer diffraction formula of a rectangular opening, x=(n+1)·λ z/a, in a case of main light, the following equation is obtained.

$$x = \lambda \cdot z/a \tag{5}$$

When the equation (5) is substituted into the equation (4), the following equation is obtained.

$$Dpd = 4 \cdot \lambda \cdot z/a(1-\cos(\theta 10))/2)^{1/2} \quad (6)$$

When the equation (6) is substituted into the equation (1), the following condition is obtained.

$$4 \cdot \lambda \cdot z/a(1-\cos(\theta 10))/2)^{1/2} \leq (L-LS)$$

Consequently, the following condition is obtained.

$$a \geq 4 \cdot \lambda \cdot z(1-\cos(\theta 10))/2)^{1/2}/(L-LS)$$

The following condition is to pass diffracted light up to $n^{th}$-order diffracted light through the interval L.

$$a \geq 4 \cdot n \cdot \lambda \cdot z(1-\cos(\theta 10))/2)^{1/2}/L-LS \quad (7)$$

Namely, when the rectangular or rhombic aperture stop member 20c having the aperture opening 20d in which the length a of the side fulfills the condition (7), $n^{th}$ order diffracted light does not illuminate the recording medium W and the head nozzle surface 1a1S of the inkjet head 1a1. It is therefore possible to reduce the amount of the offset light.

[Embodiment 2]

Figure 17:
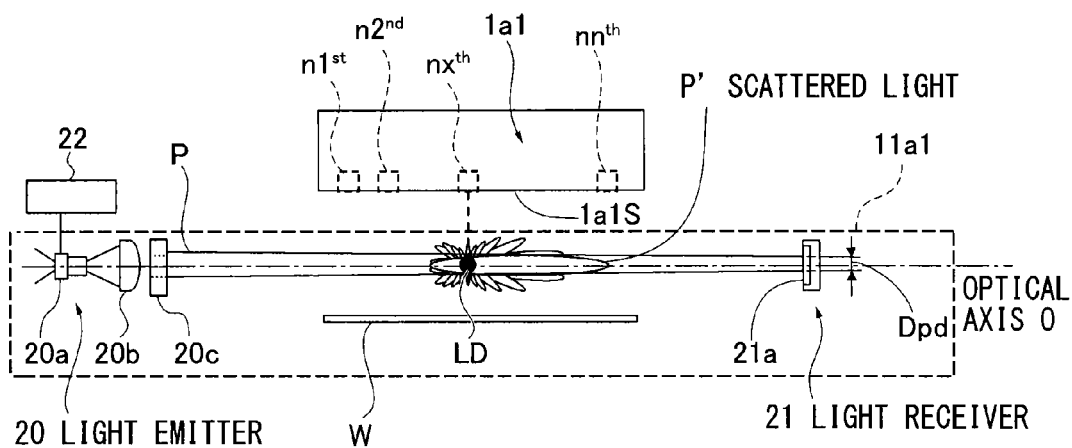
FIG. 17 is a side view schematically showing the first discharged liquid droplet-detecting device illustrated in FIG. 1 along the feeding direction of the recording medium when the light beam is a convergent light flux.
Figure 18:
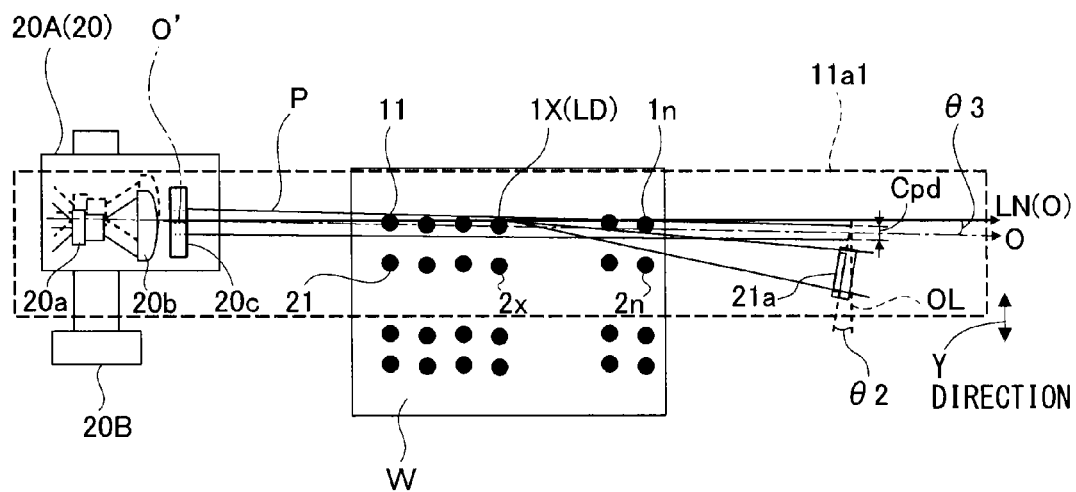
FIG. 18 is an overhead view showing the discharged liquid droplet-detecting device illustrated in FIG. 2 when the light beam is a convergent light flux.

In Embodiment 1, the condenser lens 20b constituting the light emitter 20 is configured by a collimator lens to convert the light beam P into a parallel light flux. In Embodiment 2, as illustrated in FIGS. 17, 18, the condenser lens 20b includes a convex lens to convert the light beam P into a converged light flux which is converged toward the light-receiving element from the light-emitting element.

When the light beam P is a parallel light flux, the intensity distribution of the light beam P is expanded with the influence of the diffraction by the aperture stop member 20c toward the light-receiving element from the light-emitting element. Thus, the intensity of the light beam P attenuates toward the light-receiving element from the light-emitting element, and the amount of scattered light by the liquid droplets discharged from the nozzle close to the light-receiving element is smaller than the amount of scattered light by the liquid droplets discharged from the nozzle close to the light-emitting element.

Compared to the detection accuracy of the liquid droplets discharged from the nozzle close to the light-emitting element, the detection accuracy of the liquid droplets discharged from the nozzle close to the light-receiving element deteriorates. However, with the light beam P as the converged light flux, the amount of light per unit area increases toward the nozzle close to the light-receiving element. Thus, it is possible to prevent the deterioration of the detection accuracy of the liquid droplets discharged from the nozzle close to the light-receiving element.

On the other hand, when the detection accuracy of the liquid droplet discharged from the nozzle close to the light-receiving element is appropriate, it is possible to reduce the amount of emission of the light-emitting element, to improve the safety to human eyes, and to save the electric power.

In other words, when the condenser lens 20b is configured by a lens which changes the diameter of the light beam P, it is possible to optimize the convergent rate, and it is possible to set the amount of scattered light from the liquid droplets discharged from the nozzle close to the light-emitting element to be the same as the amount of scattered light from the liquid droplets discharged from the nozzle close to the light-receiving element. Thus, it is possible to obtain the same detection accuracy (SN ratio) while reducing the amount of emission.

Although the embodiments of the present invention have been described above, the present invention is not limited thereto. It should be appreciated that variations may be made in the embodiments described by persons skilled in the art without departing from the scope of the present invention.

The discharged liquid droplet-detecting device according to the embodiments of the present invention is controlled by hardware, software, or a combination of these.

For example, when controlling the device with software, a program is installed in a memory of a computer incorporated in dedicated hardware from a recording medium in which a process sequence program is recorded. A processing sequence program is installed in a general computer, which executes various processes, to be executed.

For example, a hard disk or ROM (Read Only Memory) is used for the recording medium. For example, a process sequence program is temporarily or permanently stored in a removable recording medium. Such a removable recording medium is provided as packaged software.

The removable recording medium includes a floppy (registered trade mark) disk, CD-ROM (Compact Disc Read-Only Memory), MO (Magnet Optical) disk, DVD (Digital Versatile Disc), magnetic disc, and semiconductor memory.

The process sequence program is wirelessly transferred to a computer from a download site to be installed, or a process sequence program is transferred with a wire to a computer through a network to be installed.

According to the process ability of the image-forming apparatus and the discharged liquid droplet-detecting device, it is possible not only to execute the liquid droplet detection process in chronological order, but also to execute the liquid droplet detection process by the respective inkjet heads in parallel order or individual order.

According to the embodiments of the present invention, it is possible to prevent attachment of mist to a lens, and to improve detection accuracy of a state of a discharged liquid droplet.

What is claimed is:

1. A device for detecting a state of a discharged liquid droplet comprising:
    a plurality of nozzles which is arranged in a width direction of a recording medium orthogonal to a feeding direction of the recording medium to discharge a liquid droplet toward the recording medium;
    a light emitter which is provided on one side of the recording medium in the width direction orthogonal to the feeding direction of the recording medium; and
    a light receiver which is provided on the other side of the recording medium in the width direction, wherein
    the light emitter includes a light-emitting element, a condenser lens which condenses light from the light-emitting element to emit as a light beam, and an aperture stop member including an aperture opening through which the light beam passes,
    the aperture opening has a rhombic shape or a rectangular shape, the aperture opening having four sides that are connected at four apexes, and
    a light-receiving surface of the light-receiving element is displaced in the feeding direction of the recording medium, and is displaced on extension lines of diagonal lines of the aperture opening, the diagonal lines defined by connecting the apexes of the aperture opening which are opposite to each other and are not adjacent to each other.

2. The device according to claim 1, wherein
one of the diagonal lines of the aperture opening is parallel to the feeding direction of the recording medium,
the other of the diagonal lines of the aperture opening is vertical to the recording medium, and
diffracted light of the light beam, which is generated when the light beam passes through the aperture opening, is generated in directions of respective sides defining the contour of the aperture opening.

3. The device according to claim 1 further comprising a movement mechanism which moves the light emitter in the feeding direction of the recording medium in accordance with a position of the nozzles.

4. The device according to claim 1, wherein the condenser lens is a collimator lens which converts the light beam into a parallel light flux, or a convex lens which converts the light beam into a converged light flux.

5. The device according to claim 1, wherein the condenser lens includes a lens which changes a beam diameter of the light beam.

6. The device according to claim 1, wherein:
the light-receiving surface has a rhombic shape or a rectangular shape including four sides that are connected at four apexes, and
the four apexes of the light-receiving surface are rotated 45 degrees relative to the four apexes of the aperture opening.

7. The device according to claim 1, wherein an optical axis of the light-emitting element tilts to the arrangement direction of the nozzles.

8. The device according to claim 7, wherein the light-receiving surface of the light receiver tilts at a predetermined angle toward the light-emitting element, relative to straight light vertical to the optical axis of the light-emitting element.

9. An image-forming apparatus including the device according to claim 1.

* * * * *